US00PP07905P

United States Patent [19]

VandenBerg

[11] Patent Number: Plant 7,905

[45] Date of Patent: Jul. 7, 1992

[54] CHRYSANTHEMUM PLANT NAMED DARK TRIUMPH

[75] Inventor: Cornelis P. VandenBerg, Salinas, Calif.

[73] Assignee: Yoder Brothers, Inc., Barberton, Ohio

[21] Appl. No.: 599,350

[22] Filed: Oct. 18, 1990

[51] Int. Cl.[5] ..... A01H 5/00

[52] U.S. Cl. ..... Plt./79

[58] Field of Search ..... Plt./78, 79; 800/200

[56] References Cited

U.S. PATENT DOCUMENTS

P.P. 5,995 5/1987 Duffett et al. ..... Plt./78

4,616,099 10/1986 Sparkes ..... 800/200

*Primary Examiner*—James R. Feyrer

*Attorney, Agent, or Firm*—Foley & Lardner

[57] ABSTRACT

A Chrysanthemum plant named Dark Triumph particularly characterized by its flat capitulum form; decorative capitulum type; bronze ray floret color with a darker center of the flower creating a two-tone effect; diameter across face of capitulum of 64 to 70 mm. when fully opened; spreading and prolific branching pattern, with 6 to 9 breaks after pinch when grown outside under natural daylength in fall flowerings, and 6 to 8 breaks after pinch when grown in 10 cm. pots for spring flowerings; natural season flowering date of August 22 when planting rooted cuttings June 23 in Salinas, Calif., and September 28 to 29 when planting rooted cuttings June 15 in Hightstown, N.J.; flowering response of 43 to 46 days after rooting in no light/no shade programs in spring; plant height of 23 to 30 cm. when grown in fall under natural daylength with no growth regulators, and 18 to 20 cm. when grown in 10 cm. pots in spring with 0 to 1 applications of 2500 ppm B-9 SP; and durable, uniform performance.

1 Drawing Sheet

The present invention comprises a new and distinct cultivar of Chrysanthemum, botanically known as *Dendranthema grandiflora,* and referred to by the cultivar name Dark Triumph.

Dark Triumph, identified as 82-M22D01, is a product of a mutation induction program. The new cultivar was discovered and selected by Cornelis P. VandenBerg on July 20, 1987 in a controlled environment in Salinas, Calif., as one flowering plant within a flowering block established as rooted cuttings from stock plants which had been exposed as unrooted cuttings to an X-ray source of 1500 rads. The irradiated parent cultivar was Triumph, a flat decorative spray pot mum and garden mum in the bronze category, although its ray florets are yellow-orange. Triumph is disclosed in U.S. Plant Pat. No. 5,995.

With more specific reference to the mutation induction program resulting in the selection of Dark Triumph, three separate groups of rooted cuttings were irradiated on Jan. 8, Jan. 22 and Feb. 5, 1987 at levels of 2000, 1750 and 1500 rads, respectively. Thereafter, 129 of the plants irradiated at 2000 rads were planted Apr. 20, 1987; 446 plants irradiated at 1750 rads were planted May 11, 1987; and 577 plants irradated at 1500 rads were planted May 25, 1987. All plants were allowed to flower, and 31 original selections were made. Of these, all were eventually discarded except for Dark Triumph, which was selected Jul. 20, 1987, as noted, and the cultivar Yellow Triumph, selected on the same day. Yellow Triumph was a selection from the plants irradiated at 1750 rads. A plant patent application of applicant for Yellow Triumph is pending. Both the ray floret and flower center of Dark Triumph are substantially darker yellow-orange in color than the flower color of Triumph, and completely dissimilar to the bright yellow ray floret color of Yellow Triumph.

The first act of asexual reproduction of Dark Triumph was accomplished when vegetative cuttings were taken from the initial selection in September 1987 in a controlled environment in Salinas, Calif., by technicians working under the supervision of Cornelis P. VandenBerg.

Horticultural examination of controlled flowerings of successive plantings has shown that the unique combination of characteristics as herein disclosed for Dark Triumph are firmly fixed and are retained through successive generations of asexual reproduction.

Dark Triumph has not been observed under all possible environmental conditions. The phenotype may vary significantly with variations in environment such as temperature, light intensity and daylength.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Dark Triumph, which, in combination, distinguish this Chrysanthemum as a new and distinct cultivar:

1. Flat capitulum form.
2. Decorative capitulum type.
3. Bronze ray floret color with a darker center of the flower, creating a two-tone effect.
4. Diameter across face of capitulum of 64 to 70 mm. when fully opened.
5. Branching pattern is spreading and prolific, with 6 to 9 breaks after pinch when grown outside under natural daylength in fall flowerings, and 6 to 8 breaks after pinch when grown in 10 cm. pots for spring flowerings.

6. Natural season flower date of August 22 when planting rooted cuttings on June 23 in Salinas, Calif., and of September 28 to 29 when planting rooted cuttings June 15 in Hightstown, N.J.

7. Flowering response of 43 to 46 days after rooting in no light/no shade programs in spring.

8. Plant height of 23 to 30 cm. when grown in fall under natural daylength with no growth regulators, and of 18 to 20 cm. when grown in 10 cm. pots in spring with 0 to 1 applications of 2500 ppm B-9 SP.

9. Durable, uniform performance.

The accompanying photographic drawing is a color photograph of Dark Triumph grown as a pinched pot mum with four cuttings in a 15 cm. pot, with the colors being as nearly true as possible with illustrations of this type.

Of the commercial cultivars known to the inventor, the most similar in comparison to Dark Triumph is the parent cultivar Triumph. All traits of Dark Triumph are similar to those of Triumph, except for the ray floret color. Both the color of the outer ray florets and the inner florets near the center of the flower of Dark Triumph are substantially darker than Triumph, which are yellow-orange.

In the following description color references are made to The Royal Horticultural Society Colour Chart. The color values were determined on plant material grown as a pinched spray pot mum in Salinas, Calif. on Apr. 26, 1990. In comparing live flowering material with the photographic drawing, the colors in the photographic drawing are extremely close to the actual color of the flowers. The color of the ray florets of Dark Triumph are composed of more than one color, and cannot be described with one single value. The color values given are those believed to be closest to the actual color of Dark Triumph. The intensity of "overlaid with" cannot be described other than in relative terms.

Classification:

*Botanical.*—*Dendranthema grandiflora* cv Dark Triumph.

*Commercial.*—Flat decorative spray pot mum and garden mum.

INFLORESCENCE

A. Capitulum:

*Form.*—Flat.

*Type.*—Decorative.

*Diameter across face.*—64 to 70 mm. when fully opened.

B. Corolla of ray florets:

*Color (general tonality from a distance of three meters).*—Bronze, with a darker center of the flower, creating a two-tone effect.

*Color (upper surface).*—Outer ray florets have a base color of 20A, overlaid with 171B. Center of flower is more strongly overlaid with 171B, with the overall color of the center being closest to 168A to 168B.

*Color (under surface).*—Base color 20A, slightly overlaid with 171B.

*Color of young buds.*—Closest to 171A to 173B. Shape: Flat, straight, very slightly ribbed.

C. Corolla of disc florets:

*Color (mature).*—14A.

*Color (immature).*—144C.

D. Reproductive organs:

*Androecium.*—Present on disc florets only; very few disc florets present.

*Gynoecium.*—Present on both ray and disc florets.

PLANT

A. General appearance:

*Height.*—23 to 30 cm. when grown in fall under natural daylength with no growth regulators, and 18 to 20 cm. when grown in 10 cm. pots in spring with 0 to 1 applications of 2500 ppm B-9 SP.

*Branching pattern.*—Spreading and prolific, with 6 to 9 breaks after pinch when grown outside under natural daylength in fall flowerings, and 6 to 8 breaks after pinch when grown in 10 cm. pots for spring flowerings.

B. Foliage:

*Color (upper surface).*—147A.

*Color (under surface).*—147B.

*Shape.*—Small, lobed.

I claim:

1. A new and distinct Chrysanthemum plant named Dark Triumph, as described and illustrated.

* * * * *

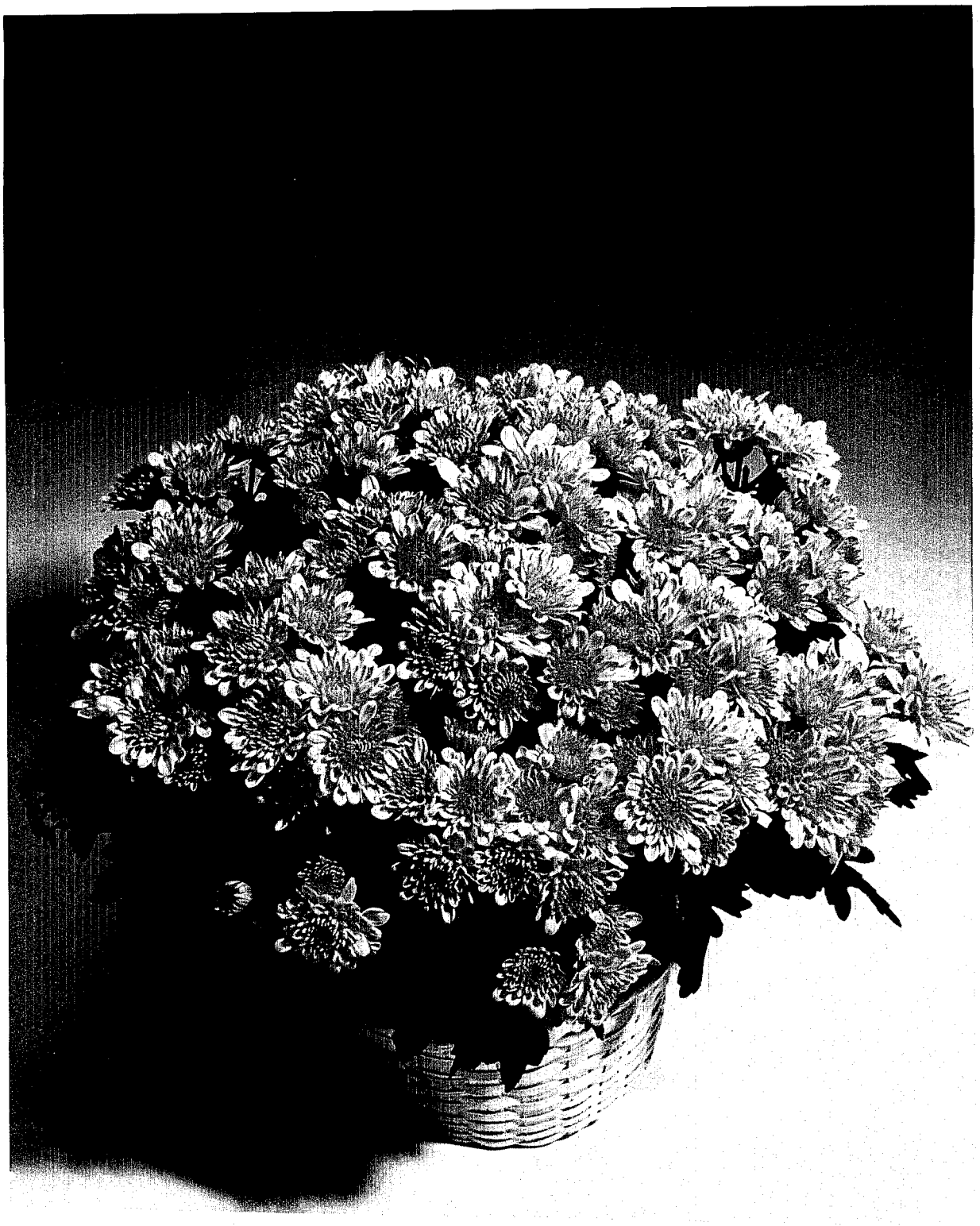

UNITED STATES PATENT AND TRADEMARK OFFICE

CERTIFICATE OF CORRECTION

PATENT NO. : PP 7,905

DATED : July 7, 1992

INVENTOR(S) : Cornelis P. VandenBerg

It is certified that error appears in the above-identified patent and that said Letters Patent is hereby corrected as shown below:

Column 1, line 18, "rooted cuttings" should read --unrooted cuttings--.

Signed and Sealed this

Sixteenth Day of November, 1993

Bruce Lehman

*Attest:*

BRUCE LEHMAN

*Attesting Officer*

*Commissioner of Patents and Trademarks*